United States Patent [19]

Mason et al.

[11] Patent Number: 4,501,414

[45] Date of Patent: Feb. 26, 1985

[54] OPERATING TABLE

[75] Inventors: Edward M. Mason, St. Louis; Murray Q. Tanner, III, Florissant, both of Mo.; Michael J. Finley, Park City, Ill.

[73] Assignee: Affiliated Hospital Products, Inc., St. Louis, Mo.

[21] Appl. No.: 464,873

[22] Filed: Feb. 8, 1983

[51] Int. Cl.[3] .................... A61F 5/00

[52] U.S. Cl. .................... 269/325

[58] Field of Search .................... 269/322-325; 128/70-74; 5/63, 66-69

[56] References Cited

U.S. PATENT DOCUMENTS

| | | | |
|---|---|---|---|
| 3,977,664 | 8/1976 | Mitchell et al. | 269/235 |
| 3,980,288 | 9/1976 | Mitchell et al. | 269/235 |
| 3,982,741 | 9/1976 | Mitchell et al. | 269/235 |
| 3,998,218 | 12/1976 | Lane et al. | 128/70 |
| 4,012,031 | 3/1977 | Mitchell et al. | 269/235 |
| 4,230,098 | 10/1980 | Vematsu | 128/71 |

*Primary Examiner*—Robert C. Watson

*Attorney, Agent, or Firm*—Senniger, Powers, Leavitt and Roedel

[57] ABSTRACT

An operating table with a table top comprising a head section, a back section, a kidney elevator section, a seat section and a leg section, mounted on a base for being raised and lowered relative to the base, slid endwise relative to the base for X-Ray or C-arm examination of a patient on the table, and tilted endwise and laterally relative to the base, the table having controls at its head end, the back section being adjustable to act either as a back or leg support and the leg section being adjustable to act either as a leg or back support for placing a patient in a sitting position with the patient's head either at the head end or foot end of the table.

9 Claims, 15 Drawing Figures

OPERATING TABLE

BACKGROUND OF THE INVENTION

This invention relates to operating tables, and more particularly to an improved operating table of the slidable-top type shown in the coassigned prior U.S. Pat. Nos. 3,977,664, 3,980,288, 3,982,741 and 4,012,031.

SUMMARY OF THE INVENTION

Among the several objects of the invention may be noted the provision of an operating table of the type shown in the said coassigned prior U.S. patents providing for X-Ray or C-Arm examination of a patient on the table top, with improvements for increasing the capability of the table to place a patient in different positions for different operations and to provide for convenient access of the operating team to the patient and to controls for the table; the provision of such an operating table with a kidney elevator for lifting a patient's mid-section for a kidney operation while retaining other table top functions; and the provision of such an operating table which enables placing a patient in a sitting position for a cervical laminectomy, for example, with the head of the patient either at the end of the table top where the table top controls are located or at the other end.

An operating table of this invention comprises a base and a table top comprising, in order from one end thereof constituting its head end to its other end constituting its foot end, a back section, a kidney elevator section, a seat section and a leg section. Means is provided mounting the table top on the base for raising and lowering it relative to the base, sliding it endwise relative to the base, and tilting its endwise and laterally relative to the base. This mounting means comprises elevator means on the base, a tilt frame mounted at the upper end of the elevator means for endwise and lateral tilting, and a slide frame mounted on the tilt frame for endwise sliding movement relative to the tilt frame and for endwise and lateral tilting relative to the base with the tilt frame. The seat section is secured to the slide frame. Hydraulic cylinder means is provided for tilting the tilt frame endwise; hydraulic cylinder means is provided for tilting the tilt frame laterally; and hydraulic cylinder means is provided for sliding the slide frame endwise relative to the tilt frame. The back section is pivotally connected at its foot end to the head end of the seat section for swinging movement of the back section between a fully lowered position angled downward from the seat section and a raised position extending up from the seat section at the head end of the seat section generally perpendicular to the seat section, hydraulic cylinder means being carried by the slide frame for swinging the back section between its said fully raised and lowered positions and maintaining it in either of these positions or in various intermediate positions of adjustment therebetween. The leg section is pivotally connected at its head end to the foot end of the seat section for swinging movement of the leg section between a fully lowered position extending down from the seat section at the foot end of the seat section generally perpendicular to the seat section and a fully raised position extending up from the seat section at the foot end of the seat section generally perpendicular to the seat section, hydraulic cylinder means being carried by the slide frame for swinging the leg section between its fully raised and lowered positions and maintaining it in either of these positions or in various intermediate positions of adjustment therebetween. Means is provided for mounting the kidney elevator section on the slide frame between the head end of the seat section and the foot end of the back section for sliding movement with the slide frame and for up and down movement relative to the slide frame between a fully lowered position generally flush with the seat section and a fully raised position elevated above the seat section, and for moving the kidney elevator section up and down and between its said fully lowered and raised positions and for maintaining it in either of said positions or in various intermediate positions of adjustment therebetween, said kidney elevator section mounting and moving means comprising a pair of supports for the kidney elevator section at opposite sides of the table mounted for up and down movement on the slide frame and hydraulic cylinder means carried by the slide frame for lowering and raising said kidney elevator section supports.

Other objects and features will be in part apparent and in part pointed out hereinafter.

BRIEF DESCRIPTION OF THE DRAWINGS

Corresponding reference characters indicate corresponding parts throughout the several views of the drawings.

DESCRIPTION OF THE PREFERRED EMBODIMENT

Figure 2:
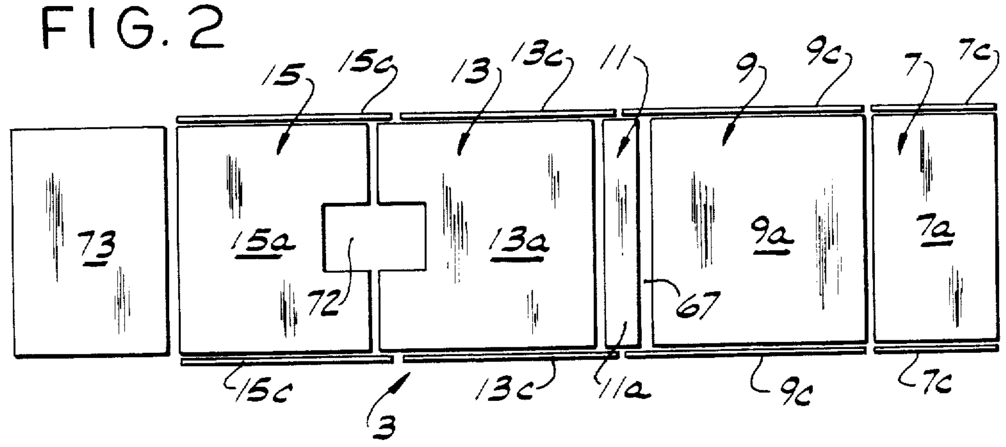
FIG. 2 is a plan of FIG. 1 showing the table top sections.

Referring to the drawings, an operating table embodying the present invention is shown to comprise a base 1, a table top generally designated 3 and means generally indicated at 5 mounting the table top on the base for raising and lowering it relative to the base, sliding it endwise relative to the base, and tilting it endwise and laterally relative to the base. The table top comprises, in order from one end constituting its head end or control end (at the right in FIGS. 1-5) to its other end constituting its foot end, a head section 7, a back section 9, a kidney elevator section 11, a seat section 13 and a leg section 15. For convenience, the end of each section toward the head or control end of the table (toward the right as viewed in FIGS. 1-5) is referred to as its head end, and its other end is referred to as its foot end. The mounting means 5 comprises elevator means generally designated 16 on the base (see FIGS. 6 and 7), a so-called tilt frame 17 mounted at the upper end of the elevator means for endwise and lateral tilting relative to the base, and a so-called slide frame or carriage 19 mounted on the tilt frame for endwise sliding movement relative to the tilt frame and for endwise and lateral tilting relative to the base along with the tilt frame, the tilt frame and carriage being adapted to be raised and lowered relative to the base by the elevator means.

The base 1 has the usual casters 21 for rolling it about, and the usual adjustable feet 23. At 24 is indicated a locking pedal for lowering the base off the casters for the feet to bear on the floor. The elevator means 16 comprises a hydraulic lift cylinder 25 extending vertically upward from the base, having a piston 27 (see FIG. 14) vertically slidable therein, and a piston rod 29 extending up from the piston through the upper end of the cylinder. A telescopic enclosure for the cylinder 25 is indicated at 33 in FIGS. 1 and 3-5 (removed in FIGS. 6 and 7). The elevator means also acts as the sole support for the table top structure. The mounting means 5 comprises a tilt frame mount generally designated 35 secured on the upper end of the piston rod, comprising a horizontal plate 37 at the upper end of the piston rod and a relatively thick triangular pivot support plate 39 extending up from plate 37 in a vertical plane offset to one side of the central vertical endwise plane of the table top. A tilt frame support or rocker beam 41 is pivoted at 43 on plate 39 for pivotal movement relative to the tilt frame mount 35 on a horizontal axis transverse to the table top for endwise tilting of the tilt frame and table top. The tilt frame 17 is an open rectangular frame having end members 45 and side members 47, and has its end members pivoted as indicated at 49 at the ends of the rocker beam 41 for pivotal movement of the tilt frame on an endwise axis for lateral tilting of the tilt frame and table top.

Figure 8:
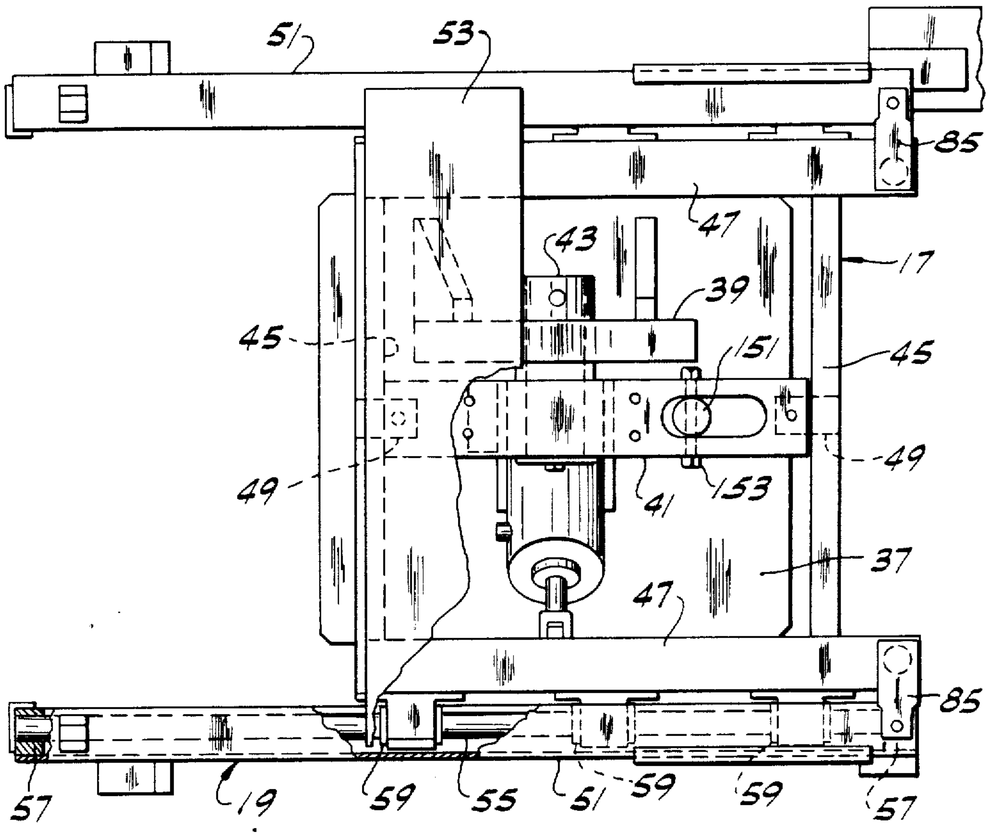
FIG. 8 is an enlarged plan of FIG. 7 with parts broken away.

The slide frame or carriage 19 comprises a pair of side channels each designated 51 and a cross-plate 53 (partially broken away in FIG. 8) spanning these channels. Each side channel has a rod 55 extending lengthwise therein, each rod being secured at its ends in fittings as indicated at 57 at the ends of the channel, the rods being axially slidable in linear ball bushings at 59 on the outside of the side members 47 of the tilt frame 17. The table top 3 is associated with the slide frame or carriage 19, and the arrangement is such that the slide frame or carriage 19 is slidable endwise within limits relative to the tilt frame 17 for the endwise sliding of the table top 3 relative to the base, with the slide frame or carriage also being adapted to be raised and lowered and tilted endwise and laterally along with the tilt frame.

Each of the table top sections 7, 9, 13 and 15 comprises a table top plate of a suitable radio-translucent material to allow for X-Ray examination of a patient on the table, and side channels supporting the plate adapted for insertion of an X-Ray cassette for X-Ray examination. The top plates of these table top sections are respectfully indicated at 7*a*, 9*a*, 13*a* and 15*a*, and the side channels of these table top sections are respectively indicated at 7*b*, 9*b*, 13*b* and 15*b*. The seat section 13 has its side channels 13*b* secured to the side channels of the slide frame 19 so that it slides endwise relative to the tilt frame 17 and the base 1 and tilts endwise and laterally relative to the base along with the tilt frame, also being adapted to be raised and lowered along with the tilt frame.

Figure 13:
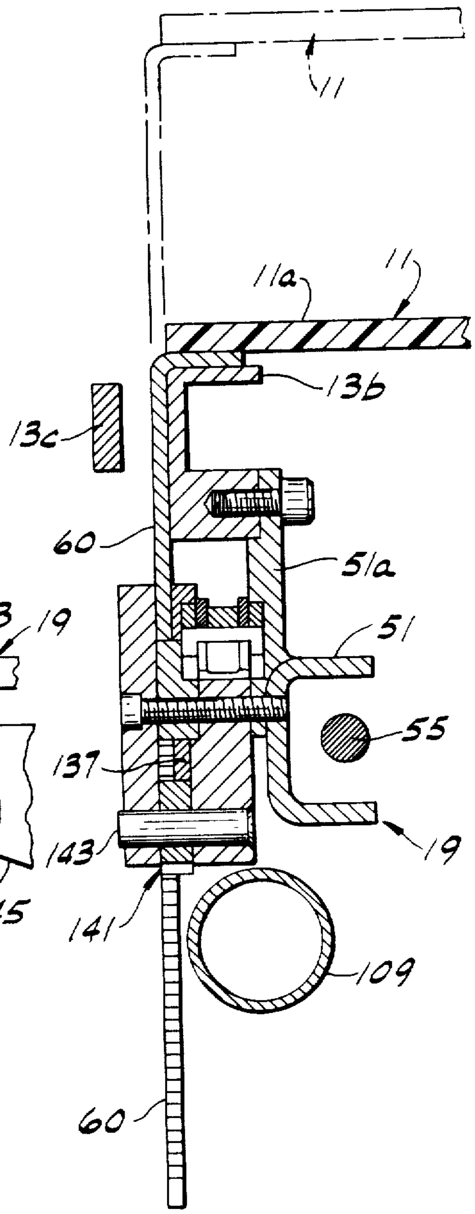
FIG. 13 is an enlarged vertical section on line 13—13 of FIGS. 9 and 11 showing in phantom a raised position of the kidney elevator section.

The kidney elevator section 11 comprises a relatively long and narrow top plate 11*a* mounted on a pair of supports each designated 60 at opposite sides of the table for up and down movement on the slide frame or carriage 19. Each of these side supports 60 is constituted by a rack which is a component of a hydraulic-cylinder-operated rack and pinion mechanism for raising and lowering the kidney elevator section as will appear. Channels such as indicated at 13*b* in FIG. 13 are secured as indicated at 51*a* to the side channels 51 of the slide frame 19.

The side channels 13*b* of the seat section 13 have extensions indicated at 61 extending beyond the top plate 13*a* of the seat section at its head end. These extensions 61 have pivot pins 63 extending laterally outward adjacent their head ends for pivotally connecting the back section 9 to the seat section. Each of the table top sections except the kidney elevator section has side rails indicated at 7*c*, 9*c*, 13*c* and 15*c*, respectively. The back section side rails 9*c* have extensions indicated at 65 extending beyond the ends of the back section side channels 9*b* at the foot end thereof (the end toward the foot end of the table top), these back section side rail extensions being pivoted on the pins 63 for pivotally connecting the back section 9 and its foot end to the head end of the seat section 13, with space 67 between the head end of the seat section top plate and the foot end of the back section top plate to accommodate the kidney elevator section top plate 11*a*. The head section 7 is suitably connected at its foot end to the head end of the back section for pivotal adjustment to various angular positions relative to the back section as may be desired and for ready removal from the back section, the detail not being critical so far as the present invention is concerned.

Pivot pins 69 extend laterally outwardly from the side channels 13*b* of the seat section 13 adjacent the foot end of the seat section. The side rails 15*c* of the leg section 15 have extensions indicated at 71 extending beyond the ends of the leg section side channels 15*b* at the head end thereof, these leg section side rail extensions being pivoted on pins 69 for pivotally connecting the leg section 15 at its head end to the foot end of the seat section 13. The seat and leg section top plates 13a and 15a may be notched as illustrated in FIG. 2 to provide what is termed a perineal cutout 72. The leg section 15 may be provided with a leg section extension 73, mounted in suitable manner for ready removal at its foot end.

The slide frame or carriage 19 is slidable on the tilt frame 17 for the endwise sliding movement four inches, for example, in head direction or foot direction from a central position, for a total stroke of eight inches. Means indicated generally at 75 for sliding it between its two end limit positions and maintaining it in either of these positions or any position therebetween including its central position is shown to comprise a pair of hydraulic cylinders referred to as the slide cylinders, each designated 77 at opposite sides of the table. Each of these cylinders is secured at its head end on the slide frame as indicated at 79 and has a piston 81 (see FIG. 14) slidable therein and a piston rod 83 extending through its piston rod end to a connection at 85 with the tilt frame 17. The two slide cylinders 77 are of the same diameter.

With the piston 27 of the table elevator cylinder 25 in its fully lowered or retracted position, the table top is at an elevation of about twenty-seven inches above the floor. The stroke of the piston 27 is such as that the table top may be raised from its lower limit of twenty-seven inches to an elevation of about forty-three inches above the floor as its upper limit.

Figure 11:
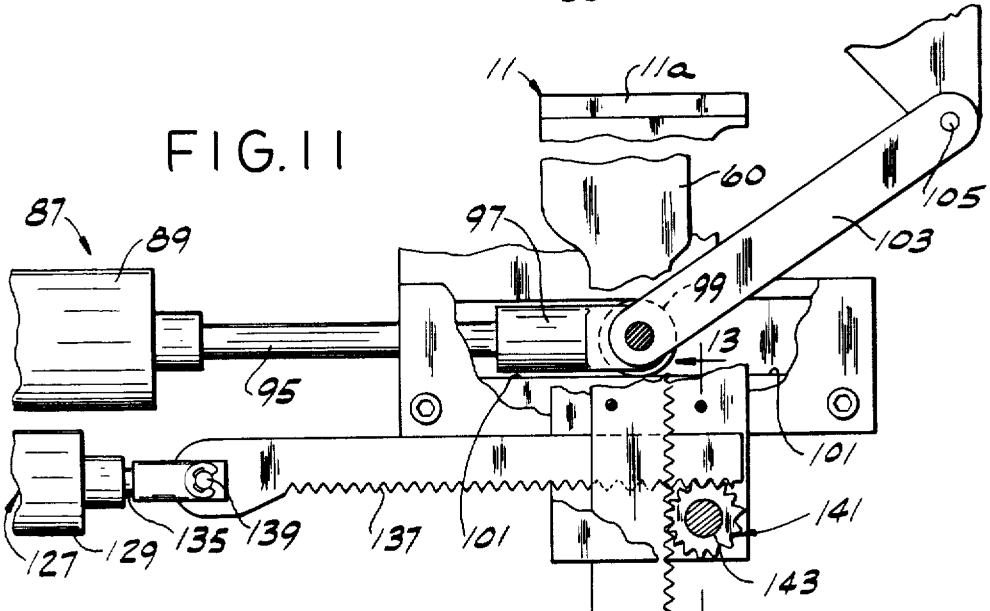
FIG. 11 is an enlarged fragment of FIG. 9 with parts broken away.

The pivotal interconnection of the back section 9 and the seat section 13 is such that the back section may be swung between a lowered position inclined downward relative to the seat section at an angle of 30° to the seat section and a raised position extending upward at an angle of 90° to the seat section. Means indicated generally at 87 for swinging the back section 9 between these limits and maintaining it in either of these limit positions or at any position therebetween, including the position in which it is shown in solid lines in FIG. 1 coplanar with the seat section, is shown to comprise a pair of hydraulic cylinders referred to as the back section cylinders, designated 89, at opposite sides of the slide frame 19. Each of these cylinders is mounted at its head end as indicated at 91 on the slide frame adjacent the foot end of the slide frame, extends toward the head end of the slide frame, and has a piston 93 (see FIG. 14) slidable therein and a piston rod 95 extending from the piston through the piston rod end of the cylinder. The two cylinders 89 are of equal diameter. At the forward end of each piston rod 95 is a fitting 95 (see FIG. 11) carrying a roller 99 rolling in a track 101 on the slide frame. A link 103 pivoted on the fitting on the axis of the roller interconnects the fitting and the back section at 105, the arrangement being such that on retraction of the piston rods 95 of cylinders 89, the back section 9 is swung down, and on extension of these piston rods, the back section is swung up. The stroke of the cylinders 89 is sufficient for the swinging of the back section from 30° down to 90° up.

Figure 9:
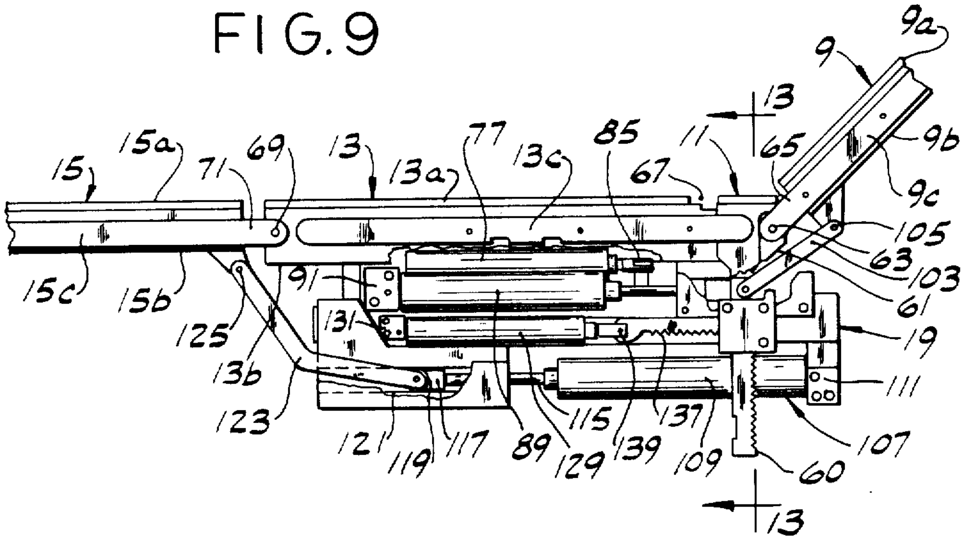
FIG. 9 is an enlarged fragment of FIG. 1 with parts broken away to show detail, showing in solid lines the back section raised.
Figure 10:
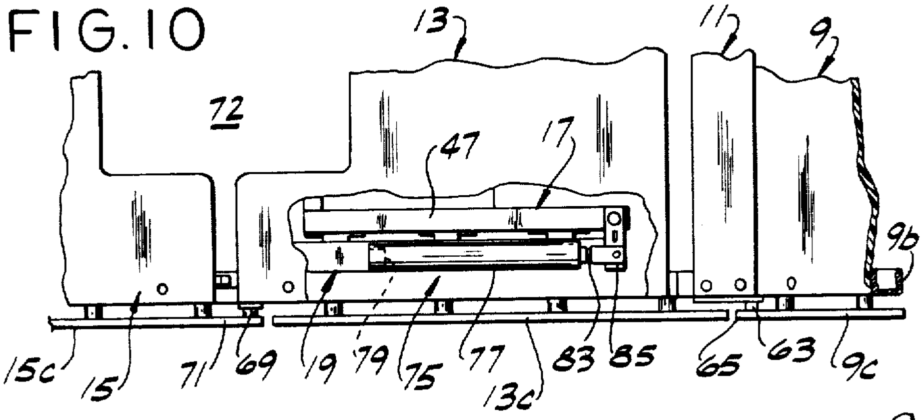
FIG. 10 is a partial plan of FIG. 9 with parts broken away.

The pivotal interconnection of the leg section 15 and the seat section 13 is such that the leg section may be swung between a lowered position extending downward relative to the seat section generally perpendicular to the seat section and a raised position extending upward relative to the seat section generally perpendicular to the seat section. The leg section may be adapted to swing down 92°, for example, from the plane of the seat section. Means indicated generally at 107 for swinging the leg section between these limits and maintaining it in either of these limit positions or at any position therebetween, including the position in which it is shown in solid lines in FIG. 1 coplanar with the seat section, is shown to comprise a pair of hydraulic cylinders referred to as the leg section cylinders, each designated 109, at opposite sides of the slide frame 19. Each of these cylinders is mounted at its head end as indicated at 111 in FIG. 9 on the slide frame adjacent the head end of the slide frame, extends toward the foot end of the slide frame, and has a piston 113 (see FIG. 14) slidable therein and a piston rod 115 extending from the piston through the piston rod end of the cylinder. The two cylinders 109 are of equal diameter. At the end of each piston rod is a fitting 117 carrying a roller 119 rolling in a track 121 on the slide frame. A link 123 pivoted on the fitting on the axis of the roller interconnects the fitting and the leg section at 125, the arrangement being such that on retraction of the piston rods 115 of cylinders 109, the leg section is swung down, and on extension of these piston rods, the leg section 15 is swung up. The stroke of the cylinders 109 is sufficient for swinging of the back section from about 90° (e.g., 92°) down to 90° up.

The kidney elevator section 11 is movable up and down relative to the seat section 13 between a lowered position wherein it is generally coplanar with the seat section (at the head end of the seat section) and a fully raised position, four and three-quarters inches, for example, above the seat section. Means 127 for moving the kidney elevator section 11 up and down between its lower and upper limits and for maintaining it at any position therebetween is shown to comprise a pair of hydraulic cylinders, referred to as the kidney elevator section cylinders, each designated 129 at opposite sides of the slide frame 19. Each of these cylinders is mounted at its head end as indicated at 131 on the slide frame, extends toward the head end of the slide frame, and has a piston 113 (see FIG. 14) slidable therein and a piston rod 135 extending from the piston through its piston rod end. The two cylinders 129 are of equal diameter. A rack 137 pinned at 139 to the end of each piston rod 135 extends toward the head end of the slide frame from the piston rod and meshes with pinion means 141 on a shaft 143 carried by the slide frame. The kidney elevator section 11 has the aforesaid pair of racks 60 extending down at opposite sides of the table in mesh with the pinion means 141 at opposite sides of the table, the arrangement being such that on retraction of the piston rods 135, racks 137 are pulled in the direction toward the foot end of the slide frame to rotate the pinion means 141 in the direction to drive the racks 60 down to lower the kidney elevator section, and on extension of the rods 135, racks 137 are pushed in the direction toward the head end of the slide frame to rotate the pinion means in the opposite direction to drive the racks 60 up to raise the kidney elevator section.

Figure 1:
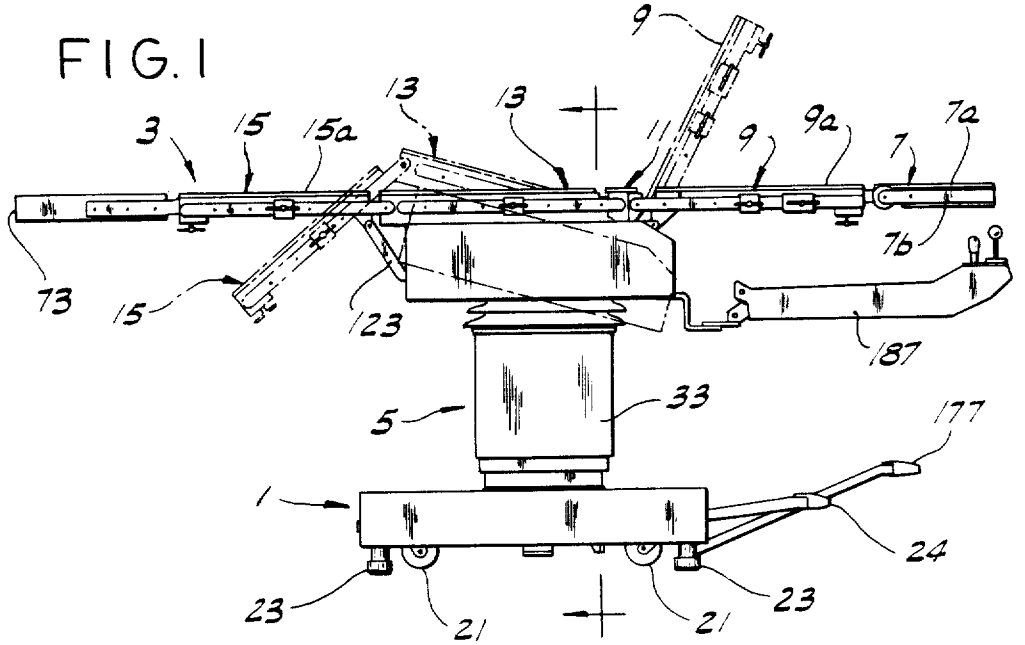
FIG. 1 is a view in side elevation of an operating table in which the improvements of this invention are embodied, showing in solid lines the head section, back section, kidney elevator section, seat section and leg section of the table top in flat coplanar position, with the top horizontal both endwise and laterally, and showing in phantom a moved position of the back, seat and leg sections constituting a first cervical laminectomy position for placing a patient in seated position with his head at the control end of the table.

Means indicated generally at 145 is provided for tilting the tilt frame 17 endwise for adjustment of the slide frame 19 and the seat section 13 (which is secured on the slide frame) through a range of positions generally from a Trendelenburg position inclined down toward its head end generally 25°, for example, to a reverse Trendelenburg position inclined up toward its head end generally at 25°, for example, and including an intermediate horizontal position (shown in solid lines in FIG. 1). This means 145 comprises a hydraulic cylinder 147, referred to as the Trendelenburg cylinder, pivotally mounted in upright position at 148 on the horizontal mounting plate 37, having a piston 149 (see FIG. 14) slidable therein and a piston rod 151 extending up through its upper end to a pin connection at 153 with the tilt frame rocker beam 41. The arrangement is such that on extension of rod 151, the tilt frame 17 is rocked counterclockwise as viewed in FIG. 7 on the pivot at 43, which may be referred to as the Trendelenburg pivot, for causing the seat section 13 to assume a reverse Trendelenburg position. On retraction of rod 151, the tilt frame is rocked clockwise as viewed in FIG. 7 for causing the seat section to assume a Trendelenburg position.

Figure 6:
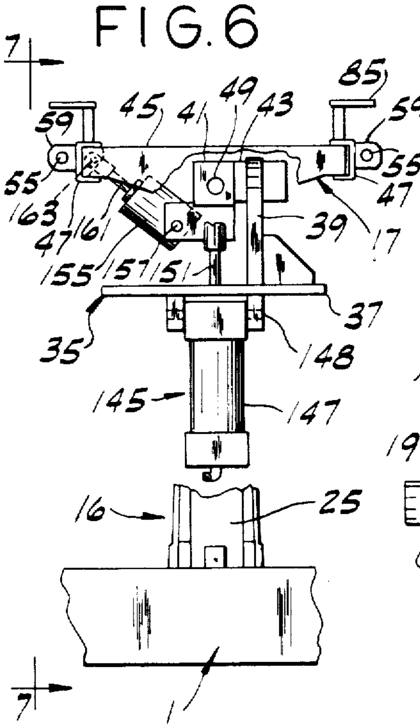
FIG. 6 is a view generally on line 6—6 of FIG. 1 on a larger scale than FIG. 1 and with parts removed and parts broken away.
Figure 7:
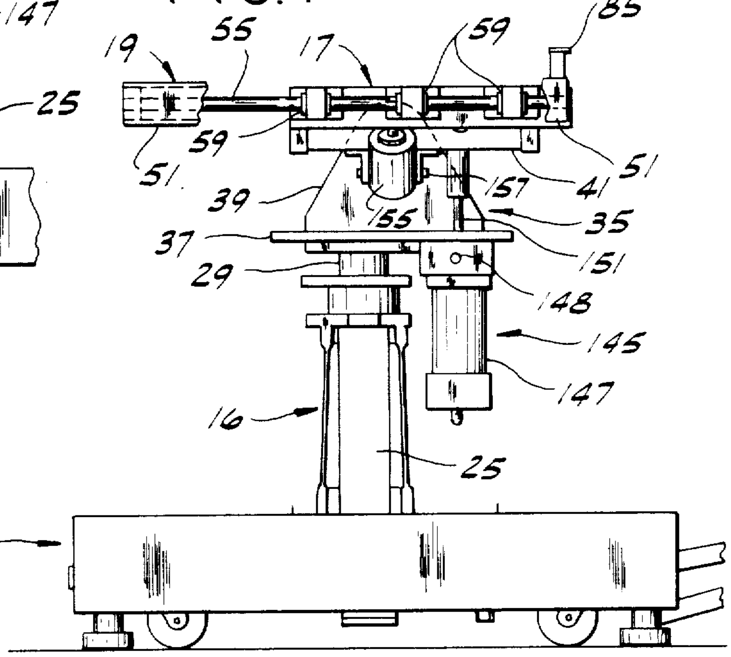
FIG. 7 is a view generally on line 7—7 of FIG. 6 with parts broken away.

Means indicated at 155 is provided for tilting the tilt frame 17 laterally for adjustment of the table top through a range of positions from a position tilted generally 17°, for example, toward the right to a position tilted generally 17°, for example, toward the left, and including an intermediate horizontal position (see FIG. 6). This means comprises a hydraulic cylinder, which may be referred to as the tilt cylinder, pivoted at its head end as indicated at 157 on the tilt frame rocker beam 41, having a piston 159 (see FIG. 14) slidable therein and a piston rod 161 extending through its other end pinned as indicated at 163 to one of the side members 47 of the tilt frame. The arrangement is such that on retraction of the piston rod 161 the tilt frame 17 and hence the table top are rocked counterclockwise as viewed in FIG. 6, and clockwise on extension of the rod.

Figure 14:
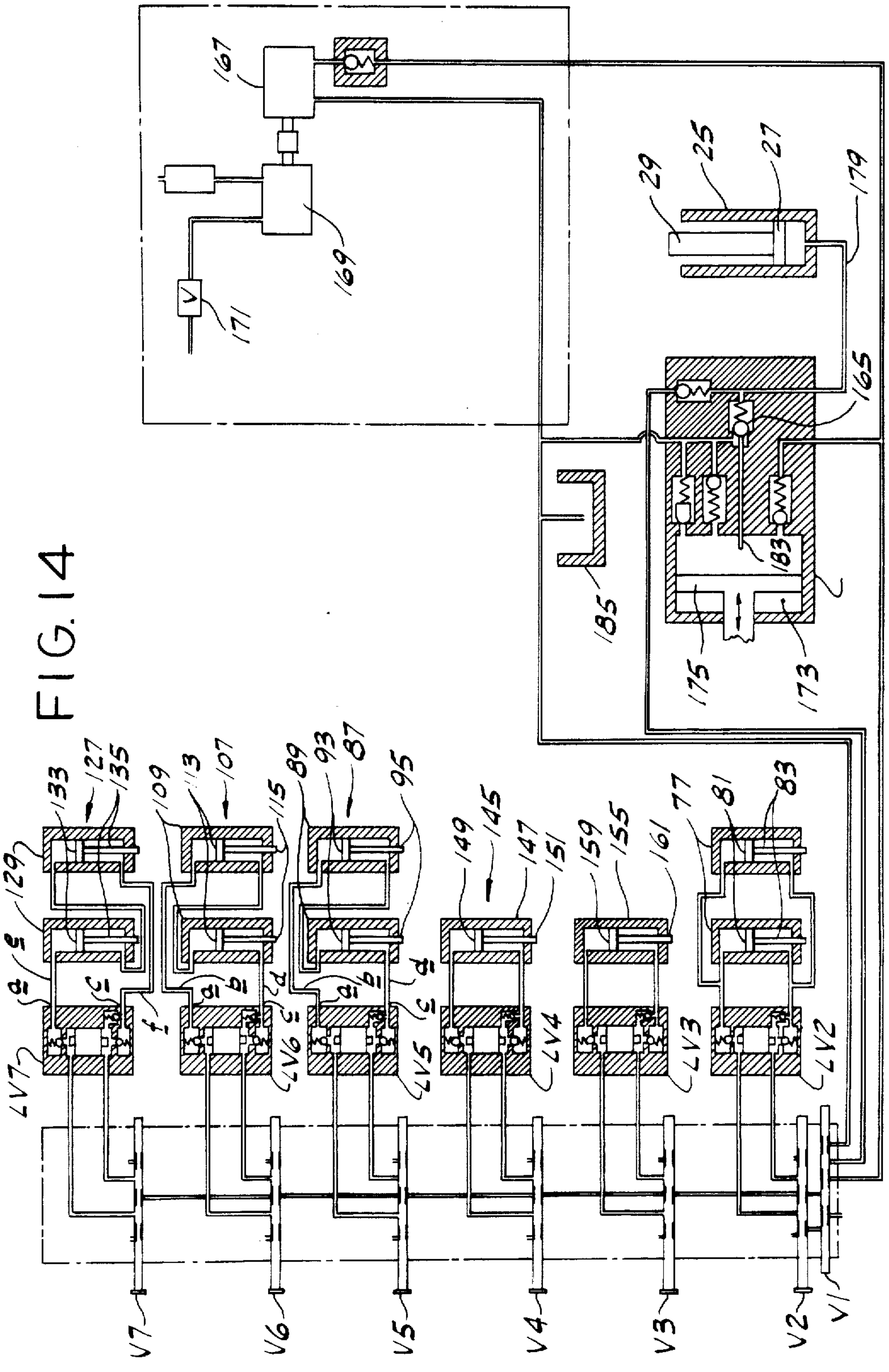
FIG. 14 is a diagram of the hydraulic circuitry for the table.

The hydraulic cylinders are all connected in a hydraulic circuit as illustrated in FIG. 14 including a foot-operated hydraulic pump 165 for pumping hydraulic fluid under pressure to the cylinders, and which may have as an additional feature for convenience a rotary hydraulic pump 167 operated by an air motor 169 under control of a pedal-operated air valve 171, for pumping hydraulic fluid under pressure to the cylinders. The foot-operated pump comprises a cylinder 173 having a piston 175 therein operable by a foot pedal 177 associated with the base 1. At 179 is indicated a line for delivery of fluid under pressure from the pump to the lower end of the lift cylinder 25 for raising the table top 3. Pump 165 has a check valve system including a descent valve 181 adapted to hold fluid under pressure in the cylinder 173 to maintain the table top 3 at any elevation to which it may be raised. Lowering of the table top 3 is effected by operating the foot pedal to push the piston 175 all the way in to actuate a rod 183 for opening the descent valve 181, which then vents fluid to a fluid reservoir 185.

A control arm 187 mounted at the head end of the slide frame 19 extends out from the latter and carries a set of valves at its outer end for controlling the raising and lowering of the table top 3, the sliding of the table top, the endwise and lateral tilting of the seat section 13, the positioning of the back and leg sections 9 and 15, and the raising and lowering of the kidney elevator section 11. The arm 187 may be mounted in such manner as to be swingable laterally and up and down through a range of positions for convenience in access to the control valves. The control arm and valve arrangement are similar to that disclosed in the aforesaid U.S. Pat. No. 3,977,664. As illustrated in FIG. 14, the set of valves comprises a valve V1 for controlling the operation of the lift cylinder 25 for raising and lowering the table top 3, a valve V2 for controlling the operation of slide cylinders 77 for the endwise sliding of the slide frame 19 and the table top 3, a valve V3 for controlling the operation of tilt cylinder 155 for the lateral tilting of the table top, a valve V4 for controlling the operation of the Trendelenburg cylinder 147 for the endwise (Trendelenburg) tilting of the seat section 13, a valve V5 for controlling the operation of the back section cylinders 89 for the positioning of the back section relative to the seat section, a valve V6 for controlling the operation of the leg section cylinders 109 for the positioning of the leg section 15 relative to the seat section, and a valve V7 for controlling the operation of the kidney elevator section cylinders 129 for the raising and lowering of the kidney elevator section 11. Valve V1, which is essentially similar to valve 261 disclosed in U.S. Pat. No. 3,977,664 is shiftable to set the system in a first mode for operation of the lift cylinder 25 by means of pump 165 for the raising and lowering of the table top 3, while blocking delivery of fluid under pressure to valves V2–V7 to inhibit their operation while the table top is being raised or lowered, and in a second mode for delivery of fluid under pressure from the pump to valves V2–V7 for their operation while inhibiting operation of lift cylinder 25 to inhibit raising and lowering of the table top.

Each of the valves V2–V7 is essentially similar to the valves 211, 221, 231, 241 and 251 disclosed in U.S. Pat. No. 3,977,664, and controls the delivery of hydraulic fluid to and return of hydraulic fluid from a so-called pilot-operated valve which is essentially similar to the pilot-operated lock valves LV101, LV71, LV111, LV121 and LV91 disclosed in U.S. Pat. No. 3,977,664 (see also U.S. Pat. No. 4,012,031). The pilot-operated valves for valves V2–V7 are here designated LV2–LV7, respectively.

The table top 3 is adapted to be raised to a desired elevation by setting valve V1 in the elevate mode and pumping hydraulic fluid, by means of the foot operated hydraulic pump 165 (or the air-motor-operated pump 167 if used), into the lower end of the lift cylinder 25. With valve V1 in its stated first or "elevate" mode, operation of all cylinders other than the lift cylinder is inhibited. Fluid is retained in the lift cylinder to hold the table top at the desired elevation. To lower it, the foot pedal 177 for the pump 165 is operated to push the piston 175 all the way in to actuate the push rod 183 to open the valve 181 to allow fluid to flow from the lift cylinder to the fluid reservoir 185.

The seat section 13 is adapted to be slid endwise one way or the other through its eight-inch range of sliding movement by setting valve V1 in its stated second mode and setting valve V2 for delivery of fluid to one of the slide cylinders 77 and return of fluid from the other via the pilot-operated lock valve LV2 to extend or retract the piston rods 83 of the slide cylinders. The lock valve LV2 functions hydraulically to lock the seat section in any position of adjustment within its eight-inch sliding range.

The table top 3 is adapted to be rocked laterally to a desired position within the range from 17° of tilt right to 17° left by setting valve V1 in its stated second mode and setting valve V3 for delivery to and return of fluid from the tilt cylinder 155 via the pilot-operated lock valve LV3 to extend (right-hand tilt) or retract (left-hand tilt) the piston rod 161 of the tilt cylinder. The lock valve LV3 functions hydraulically to lock the table top in any position of adjustment within the 17° right-17° left range.

The seat section 13 is adapted to be rocked endwise to a desired position within the range from 25° down toward its foot end to 25° up toward its foot end, including the horizontal position, by setting valve V1 in its stated second mode and setting valve V4 for delivery to and return of fluid from the Trendelenburg cylinder 147 via the pilot-operated lock valve LV4 to extend or retract the piston rod 151 of the Trendelenburg cylinder. The lock valve LV4 functions hydraulically to lock the seat section in any position of adjustment within the range of endwise pivoting of the seat section.

The back section 9 is adapted to be swung to a desired position within its range from 30° down to 90° up, including the horizontal position, by setting valve V1 in its stated second mode and setting valve V5 for delivery of fluid to one of the back section cylinders 89 and return of fluid from the other via the pilot-operated lock valve LV5 to extend (back section up) or retract (back section down) the piston rods 95 of the back section cylinders. The lock valve LV5 functions hydraulically to lock the back section in any position of adjustment within its range of swing.

The leg section 15 is adapted to be swung to a desired position within its 92° down 90° up range by setting valve V1 in its stated second mode and setting valve V6 for delivery of fluid to one of the leg section cylinders 109 and return of fluid from the other via pilot-operated lock valve LV6 to extend (leg section up) or retract (leg section down) the piston rods 115 of the leg section cylinders. The lock valve LV6 functions hydraulically to lock the leg section in any position of adjustment within its range of swing.

The kidney elevator section 11 is adapted to be raised and lowered by setting valve V1 in its stated second mode and setting valve V7 for delivery of fluid to one of the kidney elevator section cylinders 129 and return of fluid from the other via pilot-operated lock valve LV7 to extend (kidney elevator section up) piston rods 135 and racks 137, or retract (kidney elevator section down) these rods and racks. The lock valve LV7 functions hydraulically to lock the kidney elevator section in any position of adjustment within its range of up and down movement.

Figure 11A:
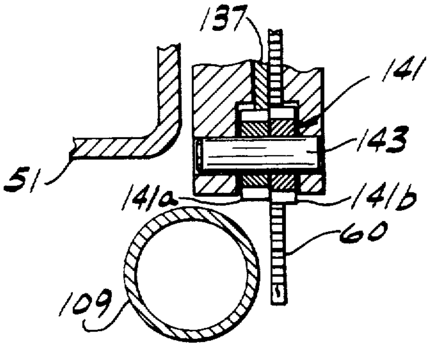
FIG. 11A is an enlarged vertical section showing a pinion means at the right-hand side of the table (right-hand as viewed looking toward the foot end of the table top)
Figure 12:
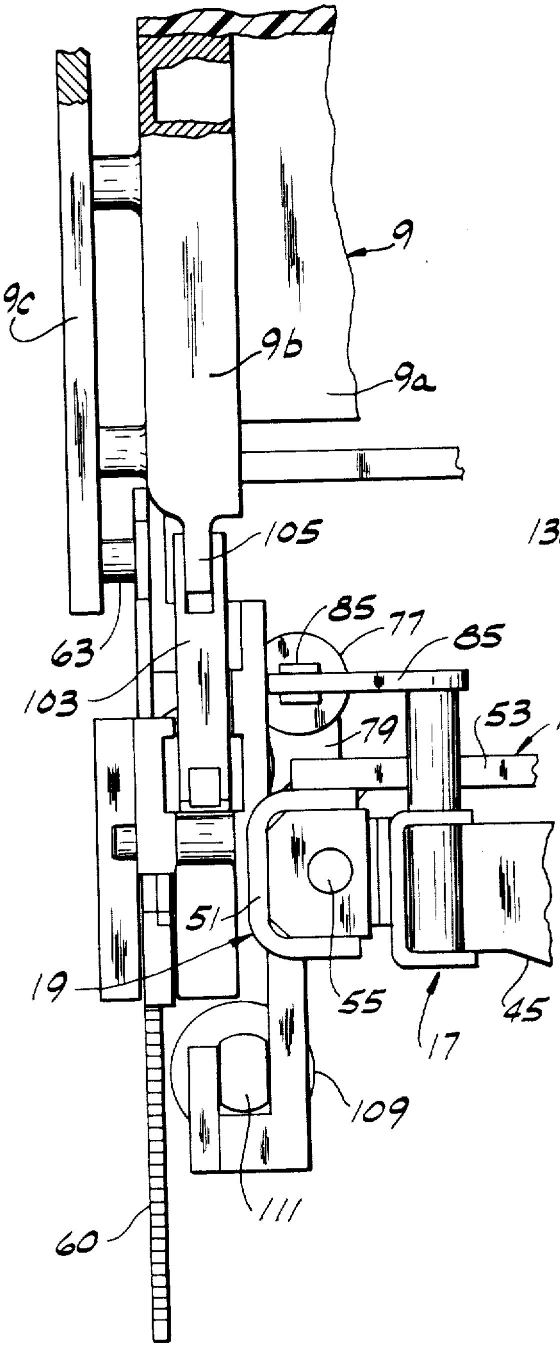
FIG. 12 is a partial end view as viewed from the right end of FIG. 9.

As illustrated in FIG. 14, the two back section cylinders 89 are hydraulically connected in tandem, the two leg section cylinders 109 are hydraulically connected in tandem, and the two kidney elevator section cylinders 129 are hydraulically connected in tandem, for operation under control of lock valves LV5, LV6 and LV7 positively to lock the sections hydraulically in any adjusted position under the loads tending to move the sections down. In this regard, each of the lock valves LV5 and LV6 has a first transfer port a interconnected as indicated at b with the head end of the respective right-hand cylinder and a second transfer port c interconnected as indicated at d with the rod end of the respective left-hand cylinder. And the lock valve LV7 has transfer port a interconnected as indicated at e to the head end of the respective left-hand cylinder and transfer port c interconnected as indicated at f to the rod end of the respective right-hand cylinder. With the tandem connection of the two back section cylinders 89, the two leg section cylinders 109, and the two kidney elevator section cylinders 129, there is differential movement of the two piston rods 95, differential movement of the two piston rods 115, and differential movement of the two piston rods 135. This is because of the difference in displacement of hydraulic fluid on the head side and rod side of each piston, the piston area being less on rod side than on the head side. The back section linkages which include links 103 are geometrically differentiated on the right and left sides in a manner similar to that disclosed in the aforesaid U.S. Pat. No. 3,982,741 involving differentiation in pin locations to compensate for differential movement of the piston rods 95 of the right and left tandem-connected back cylinders 89. The leg section linkages which include links 123 are geometrically differentiated on the right and left sides in a manner similar to that disclosed in the aforesaid U.S. Pat. No. 3,982,741 involving differentiation in pin locations to compensate for differential movement of the piston rods 115 of the right and left tandem-connected leg cylinders 109. This two kidney elevator pinion means 141 are geometrically differentiated on the right and left sides to compensate for the differential movement of the piston rods 135 of the right and left tandem-connected kidney elevator section cylinders 129. Thus, the right-hand pinion means 141 (shown in FIG. 11*a*) may comprise a first pinion 141*a* with twelve teeth driven by the right-hand rack 137 and a second pinion 141*b* with thirteen teeth driving the right-hand rack 60.

Figure 3:
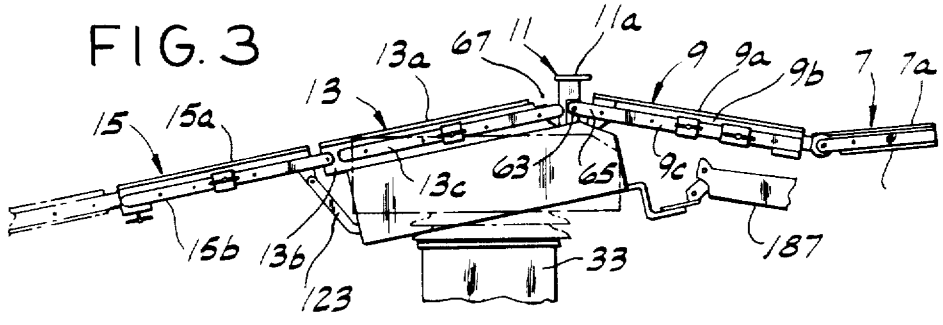
FIG. 3 is a side elevation of the table top showing a moved position of the sections for a kidney operation, the kidney elevator section being raised.
Figure 4:
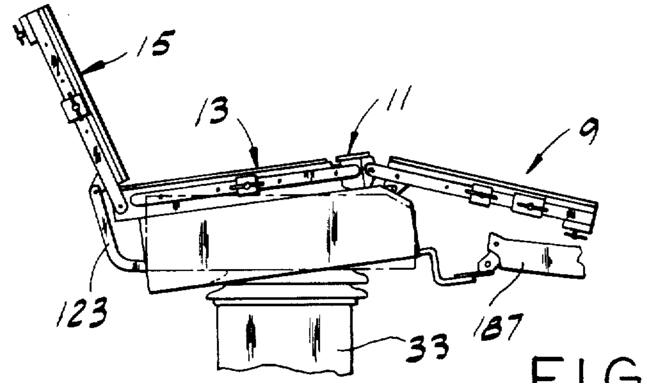
FIG. 4 is a side elevation of the table top showing a moved position of the sections constituting a second cervical laminectomy position for placing a patient in seated position with his head at the end of the table (the foot end) opposite the control end, the head section being removed.
Figure 5:
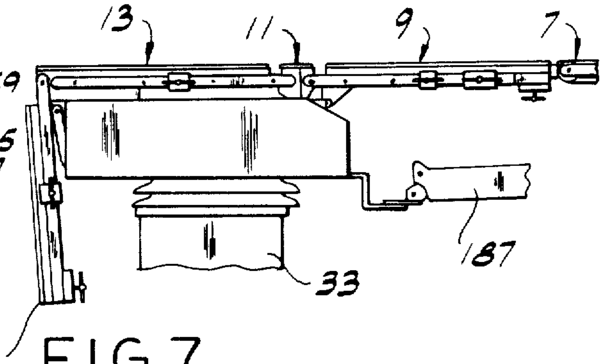
FIG. 5 is a side elevation of the table top showing a moved position of the sections for placing a patient in position for a lithotomy.

In FIG. 1, the table top sections 7, 9, 11, 13 and 15 are shown in solid lines in a flat coplanar position with the entire top 3 horizontal both endwise and laterally, as for gallbladder procedures and other abdominal procedures. Also in FIG. 1, the sections are shown in phantom lines in a moved position with the seat section 13 inclined up toward the foot end, the back section 9 up and the leg section 15 down for placing the patient in a sitting position as for a cervical laminectomy with the patient's head at the control end of the table. In FIG. 3 the sections are shown in position as for a kidney operation with the seat section 13 inclined down toward the foot end, the back section 9 inclined down toward the head end, the kidney elevator section 11 raised, and the leg section 15 coplanar with the seat section. FIG. 4 shows the table with the seat section 13 inclined up toward the head end, the back section 9 inclined down toward the head end and the leg section 15 up for placing the patient in a sitting position as for a cervical laminectomy with the patient's head at the foot end of the table. FIG. 5 shows the table with the seat section 13 and the back section 9 horizontal and the leg section 15 down for placing the patient in a supine position with the patient's legs held up in stirrups for a lithotomy procedure. In this procedure, the patient's buttocks are located over the perineal cutout 72. Many other positions are attainable.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. An operating table comprising:

a base;

a table top comprising, in order from one end thereof constituting its head end to its other end constituting its foot end, a back section, a kidney elevator section, a seat section and a leg section;

means mounting the table top on the base for raising and lowering it relative to the base, sliding it endwise relative to the base, and tilting it endwise and laterally relative to the base, said mounting means comprising:

elevator means on the base, a tilt frame mounted at the upper end of the elevator means for endwise and lateral tilting, and a slide frame mounted on the tilt frame for endwise sliding movement relative to the tilt frame and for endwise and lateral tilting relative to the base with the tilt frame;

the seat section being secured to the slide frame;

hydraulic cylinder means for tilting the tilt frame endwise;

hydraulic cylinder means for tilting the tilt frame laterally;

hydraulic cylinder means for sliding the slide frame endwise relative to the tilt frame;

means pivotally connecting the back section at its foot end to the head end of the seat section for swinging movement of the back section between a fully lowered position angled downward from the seat section and a raised position extending up from the seat section at the head end of the seat section generally perpendicular to the seat section;

hydraulic cylinder means carried by the slide frame for swinging the back section between its said fully raised and lowered positions and maintaining it in either of these positions or in various intermediate positions of adjustment therebetween;

means pivotally connecting the leg section at its head end to the foot end of the seat section for swinging movement of the leg section between a fully lowered position extending down from the seat section at the foot end of the seat section generally perpendicular to the seat section and a fully raised position extending up from the seat section at the foot end of the seat section generally perpendicular to the seat section;

hydraulic cylinder means carried by the slide frame for swinging the leg section between its said fully raised and lowered positions and maintaining it in either of these positions or in various intermediate positions of adjustment therebetween; and means mounting the kidney elevator section on the slide frame between the head end of the seat section and the foot end of the back section for sliding movement with the slide frame and for up and down movement relative to the slide frame between a fully lowered position generally flush with the seat section and a fully raised position elevated above the seat section, and comprising hydraulic cylinder means carried by the slide frame for moving the kidney elevator section up and down and between its said fully lowered and raised positions and for maintaining it in either of said positions or in various intermediate positions of adjustment therebetween.

2. An operating table as set forth in claim 1 wherein said kidney elevator section mounting and moving means comprises a pair of supports for the kidney elevator section at opposite sides of the table mounted for up and down movement on the slide frame, hydraulic cylinder means carried by the slide frame extending endwise at opposite sides thereof, and means operable by said last-named hydraulic cylinder means for lowering and raising said kidney elevator section supports.

3. An operating table as set forth in claim 1 wherein said kidney elevator section mounting and moving means comprises a pair of pinion means rotatably mounted on the slide frame adjacent its head end at opposite sides thereof, a pair of racks in mesh with said pinion means supporting the kidney elevator section, the last-named hydraulic cylinder means comprising a pair of cylinders extending endwise of the slide frame at opposite sides thereof each having a piston slidable therein and a piston rod extending through the end of the cylinder toward the head end of the slide frame, said piston rods having racks connected thereto in mesh with the pinion means.

4. An operating table as set forth in claim 3 wherein the hydraulic cylinder means for the back section and the hydraulic cylinder means for the leg section each comprises a pair of hydraulic cylinders at opposite sides of the slide frame extending endwise of the frame, each cylinder of each of the pairs for the back section, the leg section and the kidney elevator section having a piston therein and a piston rod extending from the piston, the two cylinders of each pair being hydraulically connected in tandem, said table having lock valve means for each said pair, a pair of linkages connecting the piston rods of the cylinders for the back section to the back section, a pair of linkages connecting the piston rods of the cylinders for the leg section to the leg section, the two back section linkages being geometrically differentiated to compensate for differential movement of the piston rods of the tandem-connected back section cylinders, the two leg section linkages being geometrically differentiated to compensate for differential movement of the piston rods of the tandem-connected leg section cylinders, and the two kidney elevator pinion means being geometrically differentiated to compensate for differential movement of the piston rods of the tandem-connected kidney elevator cylinders.

5. An operating table comprising:

a base;

a table top comprising, in order from one end thereof constituting its head end to its other end constituting its foot end, a back section, a kidney elevator section, a seat section and a leg section;

means mounting the table top on the base for raising and lowering it relative to the base, sliding it endwise relative to the base, and tilting it endwise and laterally relative to the base, said mounting means comprising:

elevator means on the base, a tilt frame mounted at the upper end of the elevator means for endwise and lateral tilting, and a slide frame mounted on the tilt frame for endwise sliding movement relative to the tilt frame and for endwise and lateral tilting relative to the base with the tilt frame;

the seat section being secured to the slide frame;

hydraulic cylinder means for tilting the tilt frame endwise;

hydraulic cylinder means for tilting the tilt frame laterally;

hydraulic cylinder means for sliding the slide frame endwise relative to the tilt frame; and means mounting the kidney elevator section on the slide frame between the head end of the seat section and the foot end of the back section for sliding movement with the slide frame and for up and down movement relative to the slide frame between a fully lowered position generally flush with the seat section and a fully raised position elevated above the seat section, and comprising hydraulic cylinder means carried by the slide frame for moving the kidney elevator section up and down and between its said fully lowered and raised positions and for maintaining it in either of said positions or in various intermediate positions of adjustment therebetween.

6. An operating table as set forth in claim 4 wherein said kidney elevator section mounting and moving means comprises a pair of supports for the kidney elevator section at opposite sides of the table mounted for up and down movement on the slide frame, hydraulic cylinder means carried by the slide frame extending endwise at opposite sides thereof, and means operable by said last-named hydraulic cylinder means for lowering and raising said kidney elevator section supports.

7. An operating table as set forth in claim 4 wherein said kidney elevator section mounting and moving means comprises a pair of pinion means rotatably mounted on the slide frame adjacent its head end at opposite sides thereof, a pair of racks in mesh with said pinion means supporting the kidney elevator section, the last-named hydraulic cylinder means comprising a pair of cylinders extending endwise of the slide frame at opposite sides thereof each having a piston slidable therein and a piston rod extending through the end of the cylinder toward the head end of the slide frame, said piston rods having racks connected thereto in mesh with the pinion means.

8. An operating table as set forth in claim 7 wherein the two cylinders of said pair are hydraulically connected in tandem, said table has lock valve means for said pair, and the two kidney elevator pinion means are geometrically differentiated to compensate for the differential movement of the piston rods of the said pair of tandem-connected kidney elevator cylinders.

9. An operating table comprising:

a base, a table top comprising a back section, a seat section and a leg section, one end of each section constituting its head end and the other its foot end;

means mounting the table top on the base for raising and lowering it relative to the base, sliding it endwise relative to the base, and tilting it endwise and laterally relative to the base, said mounting means comprising:

elevator means on the base, a tilt frame mounted at the upper end of the elevator means for endwise and lateral tilting, and a slide frame mounted on the tilt frame for endwise sliding movement relative to the tilt frame and for endwise and lateral tilting relative to the base with the tilt frame;

the seat section being secured to the slide frame;

hydraulic cylinder means for tilting the tilt frame endwise;

hydraulic cylinder means for tilting the tilt frame laterally;

hydraulic cylinder means for sliding the slide frame endwise relative to the tilt frame;

means pivotally connecting the back section at its foot end to the head end of the seat section for swinging movement of the back section between a fully lowered position angled downward from the seat section and a raised position extending up from the seat section at the head end of the seat section generally perpendicular to the seat section;

hydraulic cylinder means carried by the slide frame for swinging the back section between its said fully raised and lowered positions and maintaining it in either of these positions or in various intermediate positions of adjustment therebetween;

means pivotally connecting the leg section at its head end to the foot end of the seat section for swinging movement of the leg section between a fully lowered position extending down from the seat section at the foot end of the seat section generally perpendicular to the seat section and a fully raised position extending up from the seat section at the foot end of the seat section generally perpendicular to the seat section; and hydraulic cylinder means carried by the slide frame for swinging the leg section between its said fully raised and lowered positions and maintaining it in either of these positions or in various intermediate positions of adjustment therebetween, wherein the hydraulic cylinder means for the back section and the hydraulic cylinder means for the leg section each comprises a pair of hydraulic cylinders at opposite sides of the slide frame extending endwise of the frame, each cylinder of each of the pairs for the back section, and the leg section having a piston therein and a piston rod extending from the piston, the two cylinders of each pair being hydraulically connected in tandem, said table having lock valve means for each said pair, a pair of linkages connecting the piston rods of the cylinders for the back section to the back section, a pair of linkages connecting the piston rods of the cylinders for the leg section to the leg section, the two back section linkages being geometrically differentiated to compensate for differential movement of the piston rods of the tandem-connected back section cylinders, and the two leg section linkages being geometrically differentiated to compensate for differential movement of the piston rods of the tandem-connected leg section cylinders.

* * * * *